Figure 2:
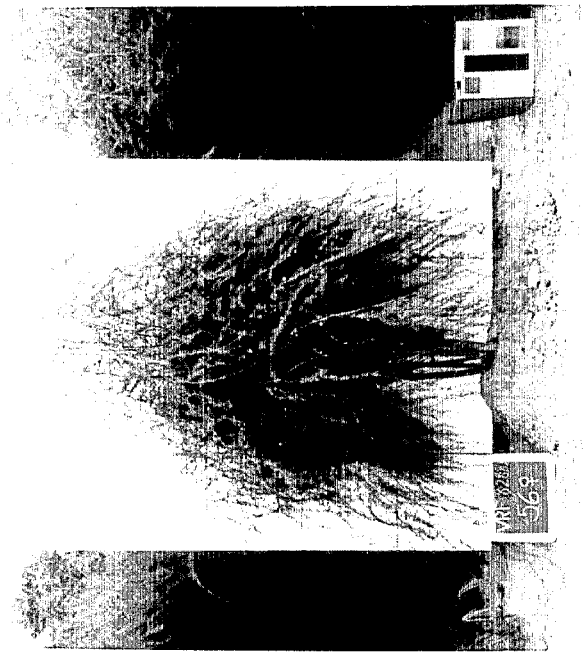

United States Patent [19]

Ellison et al.

[11] Patent Number: Plant 5,652

[45] Date of Patent: Jan. 28, 1986

[54] DISCOVERED AND ASEXUALLY REPRODUCED A CERTAIN NEW AND DISTINCT VARIETY OF ASPARAGUS PLANT

[75] Inventors: J. Howard Ellison, Milltown; John J. Kinelski, Princeton, both of N.J.

[73] Assignee: Rutgers University, New Brunswick, N.J.

[21] Appl. No.: 544,649

[22] Filed: Oct. 21, 1983

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A female asparagus plant denoted No. 56 and "Donna" developed in a program of extensive growth and selection, in turn selected from a field of the variety Mary Washington, because of its vigorous plant growth and ability to transmit disease resistance including resistance to rust (*Puccinia asparagi*) good field tolerance to root rot (*Fusarium oxysporum*) and crown rot (*F. moniliforme*) increasing production, the plant having the characteristics of a largest stalk of 31 mm diameter, number of stalks 24, and stalk vigor index (Number X (Mean diameter)$^2$) of 21,313.

2 Drawing Figures

1

The invention herein described, relates to asparagus plants and particularly to a new plant which we have developed as a desirable parent for succeeding generations.

An extensive program of asparagus plant development, carried on by us in the vicinity of New Brunswick, N.J., but not entirely limited to that area , has established a number of consistently apparent facts, particularly the aspects of transmitted characteristics.

As will be apparent the growth of plants for production as a food requires male as well as female parents and the instant invention is an example of a female plant parent which characteristically transmits some very important aspects to progeny, including disease resistance, including resistance to rust (*Puccinia asparagi*) and a good field tolerance to root and crown rot (*Fusarium oxysporum*) and (*F. moniliforme*).

Disease resistance of the kind found in our variety will enable farmers to grow hybrids where rust and fusarium now prevent profitable culture of standard susceptible varieties.

The instant plant hereunder consideration is denominated by us in our records as No. 56 and is now further identified as "Donna".

It is a vigorous plant selected by us in a ten year old field of Mary Washington asparagus near Greenwich, N.J.

We have caused our new variety to be asexually reproduced in the vicinity of New Brunswick, N.J. and find that it comes true in successive generations, and transmits the desirable characteristics previously described in our program of hybrid development. Our new variety was asexually reproduced by crown division and has subsequently been reproduced by tissue culture.

In view of our selection and growth of this particular variety, and our desire to be able to identify the same, we have accumulated data which distinguishes the same from other of the varieties which we have developed, or are known, particularly the Mary Washington (unpatented) not developed by us but which is and has been an industry standard.

The data are assembled in the table which follows:

2

ASPARAGUS PLANT NO. 56 FEMALE "DONNA"

Stalk data:

- *Number of nodes below first branch.*—32.5.
- *Number of cm from crown to first branch.*—60.7.
- *Number of branches.*—57.
- *Number cm between first and last branch.*—178.
- *Internode length in cm between branches.*—3.12.
- *Number of cladophyll nodes beyond last branch.*—36.5.
- *Number of cm beyond last branch.*—43.2.
- *Internode length in cm beyond last branch.*—1.18.
- *Largest stalk diameter in mm.*—31.0.
- *Mean diameter of three largest stalks in mm.*—29.8.
- *Number of stalks.*—24.
- *Stalk vigor index (No. X (Mean diam.)$^2$).*—21,313.
- *Mature stalk color, bloom removed.*—Color No. (1) 22–13.5.

Flower data:

- *Petal tip (yellow) Color No.* (1).—24–3.
- *Petal base (green) Color No.* (1).—21–9.5.
- *Flower length in mm.*—4.04.
- *Flower width at midpoint in mm.*—2.92.

Fruit data:

- *Weight of* 100 *fruit* (g).—20.6.
- *Water displacement of* 100 *fruit* (*ml*).—23.
- *Number of seed per* 100 *fruit.*—240.
- *Weight of seed per* 100 *fruit* (g).—6.9.
- *Water displacement of seed of* 100 *fruit* (*ml*).—9.0.
- *Mature fruit color No.* (1).—33–12.3.

Cladophyll data:

- *Number per node.*—4.60.
- *Length* (*mm*).—13.12.
- *Width* (*mm*).—0.154.

(1) Color number, Munsell Limit Color Cascade, Munsell Color, Macbeth Color and Photometry Division, 2441 Calvert Street, Baltimore, Md. 21218

Figure 1:
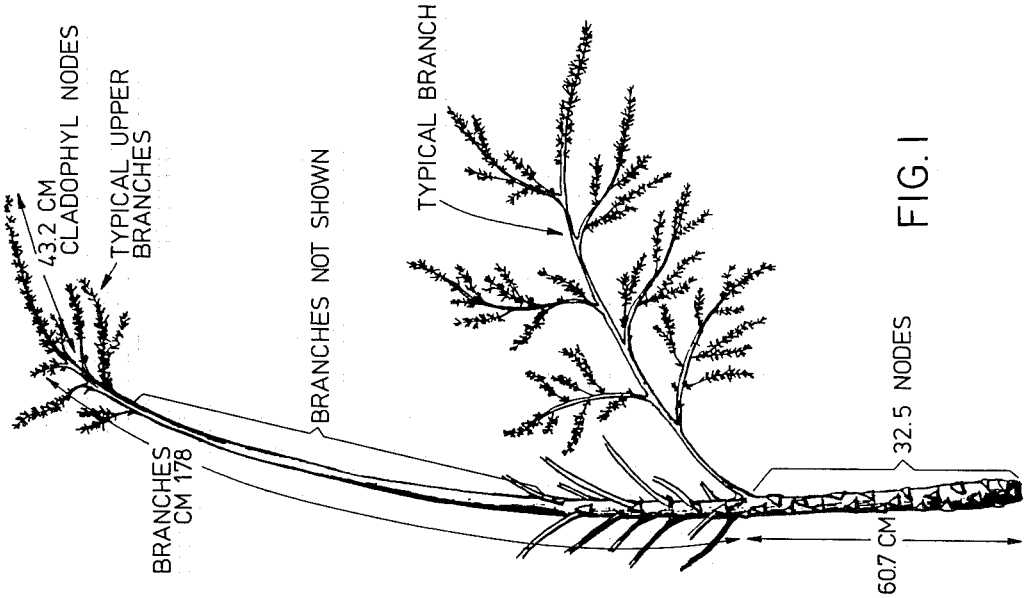

The drawing appended hereto discloses in FIG. 1, a typical stalk of our new variety with some of the data applied thereto and in black and white.

In FIG. 2, we show in color as nearly representative as is possible to make the same, a typical plant of our new variety as it appears in a field under normal conditions, the color being necessarily affected by the density of growth and reference to colors set forth as nearly true as is possible to make the same in an illustration of this kind, the color notations in our Data Summary having been selected by us from observations as compared with the Munsell Limit Color Cascade.

We claim:

1. A new and distinct variety of Asparagus Plant as herein shown and described, distinguished particularly as to novelty by its unique combination as a female plant which transmits high yield, resistance to rust (*Puccinia asparagi*) good field tolerance to root and crown rot (*Fusarium oxysporum*) and (*F. moniliforme*) provides a vigorous plant having an average of 24 stalks of mean diameter (three largest stalks) of 29.8 mm, and a stalk vigor index (Number $\times$ (Mean diameter)$^2$) of 21,313.

* * * * *